(12) United States Patent
Sugihara et al.

(10) Patent No.: US 6,281,670 B1
(45) Date of Patent: *Aug. 28, 2001

(54) TWO-DIMENSIONAL SENSOR HAVING PHOTOCONDUCTIVE LAYER FOR MEASURING CELL ACTIVITY

(75) Inventors: Hirokazu Sugihara, Katano; Makoto Taketani, Kyoto; Akihito Kamei, Nara; Hiroshi Iwasaki, Hirakata, all of (JP)

(73) Assignee: Matsushita Electric Industrial Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/661,316

(22) Filed: Jun. 13, 1996

(30) Foreign Application Priority Data

Jun. 20, 1995 (JP) .................................................... 7-153344

(51) Int. Cl.[7] .................................................. G01N 27/00
(52) U.S. Cl. .......................... 324/71.1; 324/444; 436/806
(58) Field of Search .................... 324/444, 450, 324/452, 457, 458, 501, 692, 752, 71.1, 71.5, 72; 435/29, 173.1, 173.4; 436/63, 149, 806; 128/639, 734, 741; 204/402, 406

(56) References Cited

U.S. PATENT DOCUMENTS

| | | | |
|---|---|---|---|
| 3,448,377 | * 6/1969 | Seiwatz et al. | 324/501 |
| 4,704,576 | * 11/1987 | Tributsch et al. | 324/501 |
| 4,855,243 | * 8/1989 | Simic-Glavaski | 436/63 |

FOREIGN PATENT DOCUMENTS

| | | |
|---|---|---|
| 0 300 651 | 1/1989 | (EP) . |
| 06078889A | 3/1994 | (JP) . |
| 06296595A | 10/1994 | (JP) . |

OTHER PUBLICATIONS

Nakao et al., "Scanning–laser–beam semiconductor ph–imaging sensor", *Sensor And Actuators B*, No. 2/3, Jun. 1994, Lausanne, Ch, pp. 119–123.

* cited by examiner

Primary Examiner—Glenn W. Brown
(74) Attorney, Agent, or Firm—Morrison & Foerster, LLP

(57) ABSTRACT

A two-dimensional sensor includes a photoconductive layer whose conductivity increases at a light-irradiated spot, an insulating layer formed on the front surface of the photoconductive layer, an effect electrode formed on the back surface of the photoconductive layer, and a fence as a cell holder attached to the surface of the insulating layer for containing a cell, culture medium and a reference electrode. The sensor is placed in an incubator and a bias voltage is applied between the effect and reference electrodes. When a laser beam irradiates a spot of the back surface of the sensor, a signal is obtained from the effect electrode. This signal corresponds to a potential alteration due to the cell activity substantially at the laser-irradiated spot. The signal is processed in a computer. The beam spot size and location, corresponding to the size and the location of the measurement electrode, can be changed or adjusted easily by focusing or moving the laser beam.

10 Claims, 4 Drawing Sheets

TWO-DIMENSIONAL SENSOR HAVING PHOTOCONDUCTIVE LAYER FOR MEASURING CELL ACTIVITY

FIELD OF THE INVENTION

The present invention relates to a two-dimensional sensor and a measurement system using the sensor for measuring cell activities. The sensor detects a potential alteration due to a cell activity.

BACKGROUND OF THE INVENTION

Medical research of nerve cells and research for the possibility of using nerve cells as electric devices are being made widely. When nerve cells become active, an action potential is generated. Ion density inside and outside of a nerve cell varies at first due to the alteration of the ion transparency, then the potential of the cell membrane alters. Therefore, it is useful to measure a two-dimensional distribution of the potential of the cell membrane for observing a sample cell or an tissue. Measuring two-dimensional distribution of the potential provides a method for determining an active part and a level of the activity.

The inventors have developed an integrated combination electrode as the two-dimensional sensor that can be used for measuring cell membrane potentials of plural spots simultaneously without insertion of glass electrodes or other stimulating electrodes into the cell (Japanese Tokukaihei 6-78889, 6-296595). This integrated combination electrode includes many micro electrodes arranged in matrix and their lead pattern formed on a glass plate using conductive substances, on which a sample cell or an tissue can be cultivated. This integrated combination electrode enables measuring potential alterations of plural spots in smaller pitch than glass electrodes or other conventional means. Furthermore, this integrated combination electrode enables long term observation of the sample cell or the tissue that are cultivated on the integrated combination electrode.

However, this integrated combination electrode is not suitable for an extensive use since it has a fixed size and a fixed pitch of measuring electrodes. In other words, it is difficult to use one integrated combination electrode for measuring different samples. In fact, different integrated combination electrodes were made by adjusting the size and pitch of electrodes to different samples.

SUMMARY OF THE INVENTION

A two-dimensional sensor and a measurement system using the sensor are described that are suitable for an extensive use of measuring cell activities of different samples, by improving the above integrated combination electrode, and making the size and the pitch of the electrodes changeable.

The two-dimensional sensor according to the present invention is a board-like sensor. The sensor has a photoconductive layer whose conductivity increases at the light-irradiated spot, an insulating layer formed on the front surface of the photoconductive layer, and an effect electrode formed on the back surface of the photoconductive layer. On the surface of the insulating layer, a cell holder is attached for holding a sample cell, culture medium, and a reference electrode. When a potential alteration occurs due to a cell activity, a signal obtained from the effect electrode substantially corresponds to a potential alteration at the spot irradiated by the light beam.

The photoconductive layer can be made of semiconductor such as selenium, CdS, Ge—Si or other intrinsic semiconductor. Alternatively, the photoconductive layer can be made of photoconductive polymer. A condensed polycyclic aromatic hydrocarbon such as anthracene, a heteroaromatic cycle such as carbazole, or an aryl-amine can be used as a photoconductive group included in side chains or principal chains of the polymer. Alternatively, an organic thin film such as vaper-deposited phthalocyanine thin film or Me-PTC (methylenperilene-carboxylic acid) that is a perilene pigment can be used.

Using the two-dimensional sensor of the present invention, and irradiating a spot of the photoconductive layer, a signal can be detected that corresponds to potential alteration of a part of the cell. This part is contacted with the spot mentioned above of the photoconductive layer. Since conductivity of the photoconductive layer increases only at the spot irradiated by the laser beam, the detected signal corresponds substantially to the potential alteration of the cell part contacted with the laser-irradiated spot of the sensor.

Therefore, the location of the laser-irradiated spot that corresponds to the measurement electrode can be changed by moving the laser beam. The size of the spot (i.e., the size of an electrode) can also be changed by focusing the laser beam. Since the insulating layer exists between the photoconductive layer and the cell, cell membrane potential itself is difficult to detect. However, an alteration of the potential, that is, an AC or pulse component of the potential can be detected. Therefore, the cell activity can be measured by the alteration of the potential.

A measurement system of the present invention comprises the two-dimensional sensor mentioned above, a laser beam source for irradiating a spot on the back surface of the two-dimensional sensor with a laser beam, a DC power source for applying a DC bias voltage between the effect electrode on the back surface of the two-dimensional sensor and the reference electrode in the cell holder on the front surface of the two-dimensional sensor, and means for processing a signal obtained between the two electrodes.

It is advantageous to use a laser beam for irradiating a spot of the sensor as a laser can be focused in a pinpoint spot easily.

It is preferable that the measurement system includes means for maintaining an environment for cultivating the sample cell in the cell holder on the sensor. The maintaining means enables long-term observation of the sample.

It is also preferable that the system further comprises means for scanning the laser beam emitted from the laser beam source, at high speed in the predetermined area of the back surface of the two-dimensional sensor. Thus cell activities in plural spots are measured substantially at the same time. Instead of scanning one laser beam, a laser array that comprises a plurality of laser elements arranged in a matrix can be used. By driving th e plurality of laser elements with a time-sharing method, faster scanning can be performed. Instead of moving the laser beam, the two-dimensional sensor can be moved so as to change the laser-irradiated spot of the sensor. In this case, the system may comprise an X-Y stage that controls the horizontal position of the two-dimensional sensor.

DETAILED DESCRIPTION OF THE PREFERRED EMBODIMENTS

Figure 1:
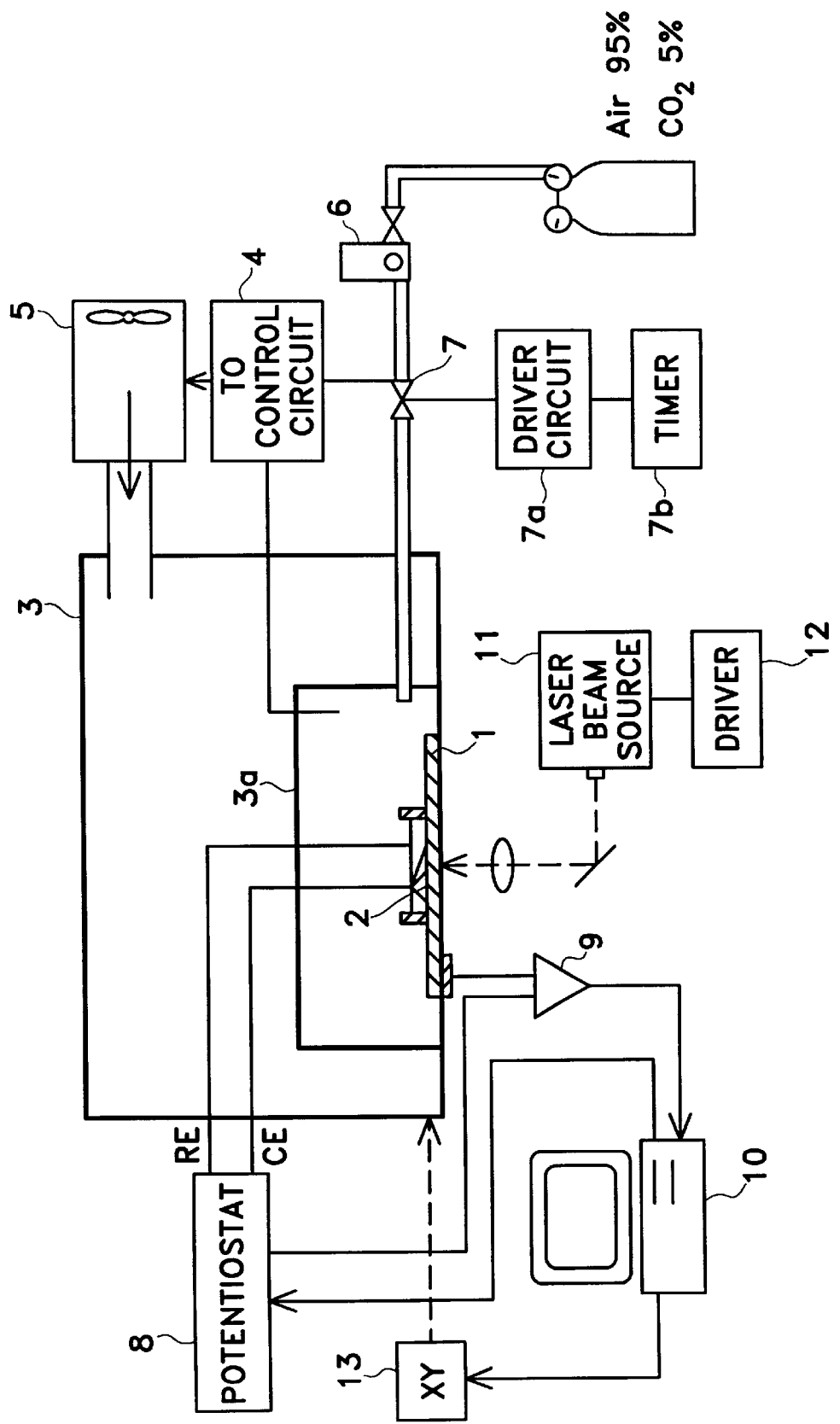
FIG. 1 is a block diagram of a cell activity measurement system using a two-dimensional sensor of the present invention.

A preferred embodiment of a measurement system for measuring cell activities according to the present invention is shown in FIG. 1. On the two-dimensional sensor 1, a sample cell 2 and its culture medium are placed. The two-dimensional sensor 1 including the sample 2 and the culture medium is set in an incubator 3.

Figure 2A:
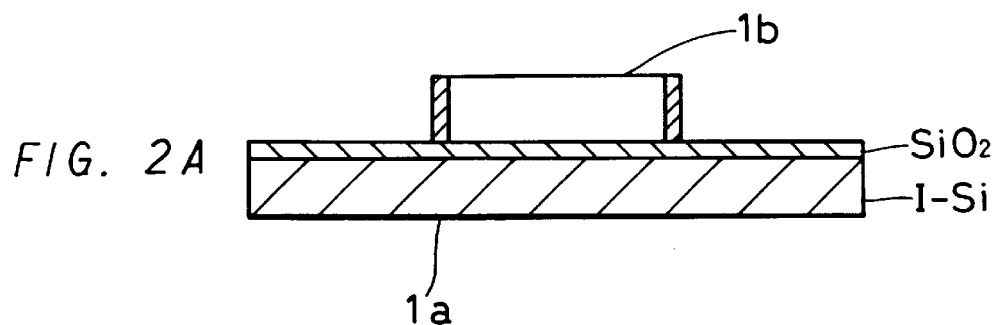
FIG. 2A and 2B show a cross section and a plane view of the two-dimensional sensor used in the measurement system in FIG. 1.
Figure 2B:
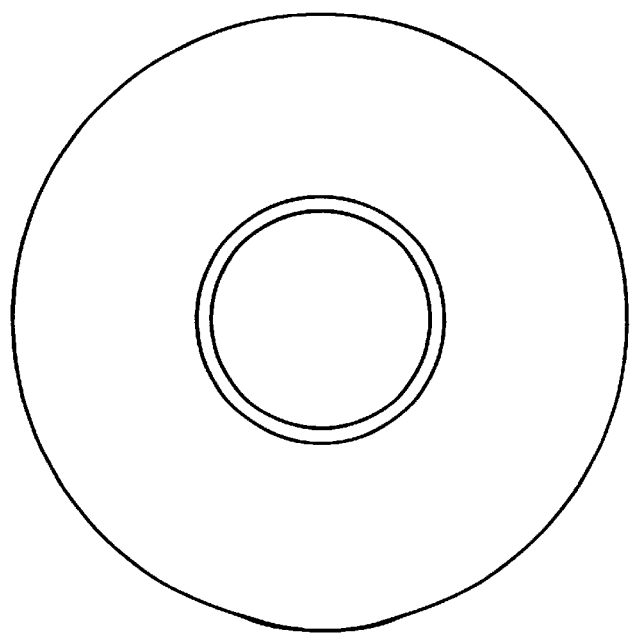

As shown in FIGS. 2A and 2B, the two-dimensional sensor 1 has a structure consisting of a substrate made of intrinsic silicon as a photoconductive layer, a gold-antimony thin film 1a that makes an effect electrode formed on the back surface of the substrate, and $SiO_2$ layer as an insulating layer formed on the front surface of the substrate. On the $SiO_2$ layer, a fence 1b is attached as a cell holder that contains a cell, culture medium and a reference electrode. FIG. 2A is drawn wit h exaggeration in the vertical direction. For example, total thickness of the sensor is about 200 $\mu$m. The intrinsic silicon substrate was polished specularly on both sides. A gold-antimony thin film 1a formed on the back surface by vapor deposition became an alloy at 500° C. so as to make an ohmic contact. The fence 1b for containing a cell and o ther things has a cylindrical shape made of polycarbonate whose inside diameter is, for example, 26 mm, which is adhered to the insulating layer on the substrate. For easy handling, an aluminum frame was attached to this sensor.

In FIG. 1, the incubator part 3 has a double-wall structure for ensuring protection of the inside from infection by outside germs. A temperature control unit 4 controls a heater and a fan unit 5 according to an output of a temperature sensor, so as to maintain the sample room 3a of the incubator part 3 at a constant temperature, e.g., 37±0.5° C. A mixed gas consisting of 95% air and 5% $CO_2$ is fed into the sample room. The conduit of the mixed gas has a flow meter 6 and an electromagnetic valve 7. The system has a drive circuit 7a for driving the valve 7 as well as a timer 7b that controls the drive circuit 7a. The incubator part 3, the temperature control unit 4, and other parts constitute the cultivating means.

The system includes a potentiostat 8 for applying a bias voltage between the reference electrode (RE) in the fence of the sensor and the effect electrode on the back surface of the sensor. The current signal between the above electrodes is led into an amplifier 9, in which the signal is amplified and passed to a computer 10. The computer includes a 16 bit A/D converter.

There is a correspond electrode (CE) within the fence of the sensor; the CE as well as the reference electrode (RE) is connected to the potentiostat 8. The CE is used for stimulating the sample by contacting with the same in the fence of the sensor so as to measure an evoked potential generated by the sample. For this purpose, a pulse voltage is applied between the RE and the CE. This stimulating voltage (pulse voltage) is generated by the potentiostat 8 according to the instruction from the computer 10. The system can also measure a spontaneous discharge without applying any stimulations.

In FIG. 1, a laser beam source 11 and its driver 12 are illustrated. The laser beam source 11 irradiates a spot of the back surface of the two-dimensional sensor with a laser beam. The laser beam emitted from the laser beam source 11 is focused by an optical system including a mirror and a lens (an object lens of an inverted microscope was used). The beam may be focused into a spot having a diameter on the order of a micron.

The system further comprises an X-Y stage 13 as means for changing a location of the laser-irradiated spot in the back surface of the sensor. The X-Y stage 13 moves the two-dimensional sensor contained in incubator 3 in the horizontal direction. The X-Y stage 13 has stepping motors controlled by the computer 10 so as to control the position of the sensor by a step of 1 $\mu$m.

The position of the laser beam is fixed while the position of the two-dimensional sensor 1 is changed in the above embodiment. However, it is more preferable to scan the laser beam and to fix the position of the two-dimensional sensor 1. An X-Y galvano-mirror may be used in the optical system for scanning of the laser beam. An alternative method for scanning the laser beam may use a laser array that consists of many laser elements arranged in a matrix. In this method, each laser element emits a laser beam perpendicularly to the back surface of the sensor and the laser elements are driven with a time-sharing method.

As mentioned before, a laser-irradiated spot of the two-dimensional sensor 1 generates hole and electron pairs. Thus a photocurrent is forced to flow by the bias voltage between the reference electrode and the effect electrode. A stable current can not flow since an insulator layer ($SiO_2$) is formed on the front surface of the two-dimensional sensor, but an alternating current, especially a pulse current can flow. Therefore, an alteration of the potential generated by the spontaneous discharge of the cell can be detected as a pulse current. Moreover, an action potential of the cell may be evoked by a stimulating pulse applied between the correspond electrode (CE) and the reference electrode (RE).

An experiment example will be explained as follows, where a nerve cell may be activity of rat brain slice was monitored using the above measurement system. The brain of SD rat (Sprague Dawley rat) 2 days old was dissected; a part of a visual area of the brain was cut in a 0.5 mm thickness sample. This sample was cultured in the fence of the two-dimensional sensor. For enhancement of the adhesive property, the insulating layer on the surface of the sensor was processed with polylysine and DF+f was used as the culture medium. 'DF' is a mixture of DMEM and F-12 Nutrient Mixture mixed by the ratio of 1:1; 'f' is a mixture of insulin 5 $\mu$g/ml, transferring 100 $\mu$g/ml, progesterone 20 nM, hydrocortisone 20 nM, putresine 100 $\mu$M, selenium 20 nM, and fetal calf serum 5%.

Figure 3:
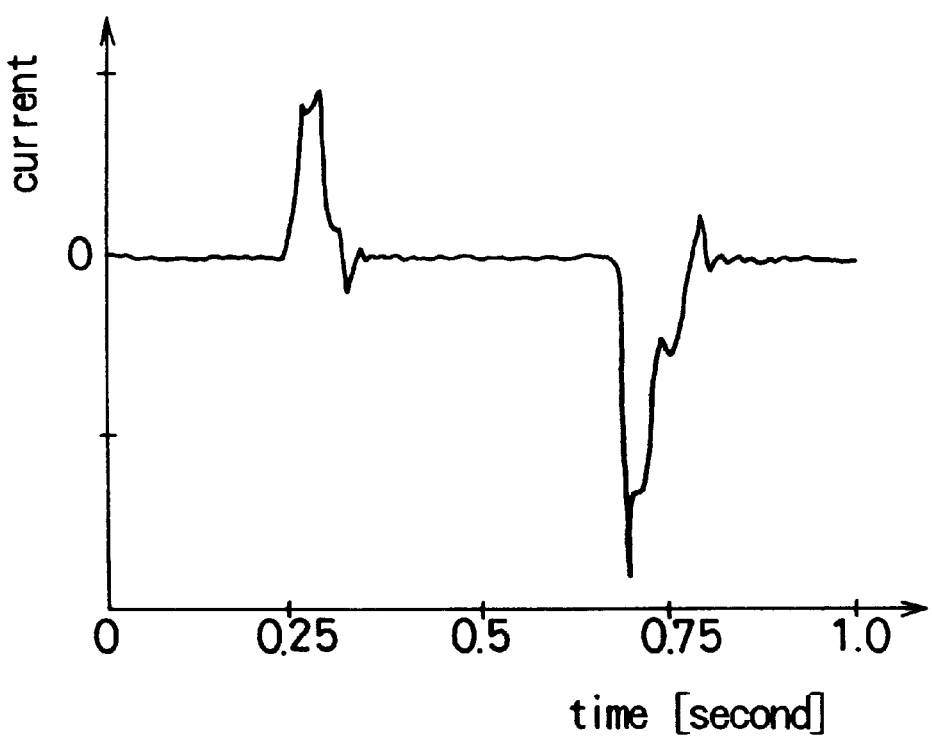
FIG. 3 illustrates an example wave form of a transitional current that corresponds to a cell activity to be detected.
Figure 4:
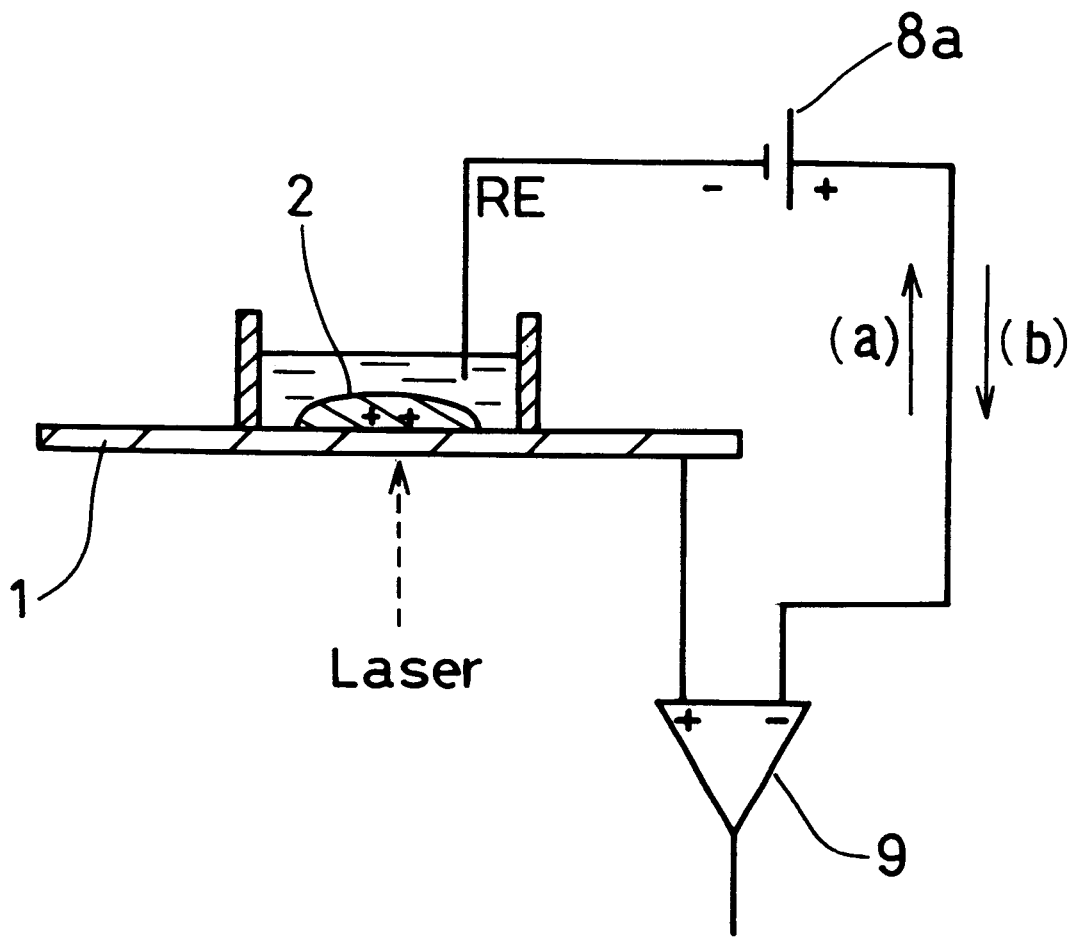
FIG. 4 is a schematic of a circuit in which a transitional current flows concerning the measurement system in FIG. 1.

The above sample generated a spontaneous discharge seven or ten days after starting of the cultivation. FIG. 3 illustrates electric activities of the sample, that is a transitional current detected by the measurement system. In FIG. 3, two transitional currents are seen; one is a positive pulse current around 0.25 second and another is a negative pulse current around 0.7 second. FIG. 4 shows a simplified circuit of the measurement system in which the transitional current flows. In this figure, 8a represents the bias voltage applied between the reference electrode (RE) and the effect electrode (via an amplifier 9) by the potentiostat 8. The following hypothesis follows from FIGS. 3 and 4.

At around 0.25 second in FIG. 3, the positive potential was generated by the spontaneous discharge of the cell. The polarity of the potential was positive with respect to the potential of the culture medium, in which the reference electrode was dipped; the potential caused a transitional current in the direction (a) in FIG. 4. After that, the positive potential disappeared around 0.7 second when a transitional current flowed in the direction (b) in FIG. 4.

Therefore, it is supposed that the depolarization of the cell membrane, which caused the positive change of the cell membrane potential, lasted for approximately 0.45 second. When the location of the laser-irradiated spot is changed, similar transitional currents were detected in the spot where the spontaneous discharge was considered to be generated due to the cell activity.

As explained above, the two-dimensional sensor of the present invention comprises a photoconductive layer, an effect electrode and an insulating layer on which a sample can be cultivated in the fence. By irradiating a spot on the back surface of the sensor with a laser beam, a cell membrane potential alteration due to a cell activity in the spot can be detected. Therefore, the size and the location of the laser beam spot, corresponding to the size and the location of the measurement electrode respectively, can be changed easily by focusing or moving the laser beam relative to the sensor.

What is claimed is:

1. A measurement system for measuring an active electrical cell activity, the system comprising:
   a two-dimensional sensor comprising a photoconductive layer, an insulating layer formed on a front surface of the photoconductive layer, an effect electrode formed on a back surface of the photoconductive layer, and a cell holder disposed adjacent the insulating layer for containing a cell, culture medium and a reference electrode;
   a constant laser beam source for constantly irradiating a spot on the photoconductive layer with a laser light beam during measurement of the active electrical cell activity;
   a DC power source for applying a IDC bias voltage between the effect electrode on the back surface of the photoconductive layer and the reference electrode in the cell holder on the front surface of the photoconductive layer; and
   and wherein an active electrical cell activity signal is obtained from the effect electrode when said laser light beam irradiates said spot, and wherein the signal corresponds to an electrical potential alteration substantially at the spot irradiated by the laser light beam and to said active electrical cell activity.

2. The measurement system according to claim 1, the system further comprising means for maintaining an environment for cultivating the cell in the cell holder on the sensor.

3. The measurement system according to claim 1, the system further comprising means for scanning the laser beam emitted from the laser beam source in a predetermined area of the back surface of the photoconductive layer.

4. The measurement system according to claim 1, the system further comprising a laser array that includes a plurality of laser elements arranged in matrix, each laser element emitting a laser beam perpendicular to the back surface of the photoconductive layer.

5. The measurement system according to claim 1, the system further comprising an X-Y stage that controls horizontal position of the two-dimensional sensor for changing a location of the laser-irradiated spot on the sensor.

6. A measurement system for measuring an active electrical cell activity, the system comprising:
   a two-dimensional sensor comprising a photoconductive layer whose conductivity increases when irradiated with light, an insulating layer formed on a front surface of the photoconductive layer, an effect electrode formed on a back surface of the photoconductive layer, and a cell holder disposed adjacent the insulating layer for containing a cell, culture medium and a reference electrode;
   a constant laser beam source for constantly irradiating a spot on the photoconductive layer with a laser beam during measurement of an active electrical activity;
   wherein an active electrical cell activity signal is obtained from the effect electrode when said laser beam irradiates said spot, and wherein the signal corresponds to an active electrical potential alteration substantially at the spot irradiated by the laser beam and to said active electrical cell activity, and
   a processor for measuring both positive and negative electrical signals obtained from said cell and measured between the effect and reference electrodes.

7. The measurement system according to claim 6, the system further comprising means for maintaining an environment for cultivating the cell in the cell holder on the sensor.

8. The measurement system according to claim 6, the system further comprising means for scanning the laser beam emitted from the laser beam source in a predetermined area of the back surface of the photoconductive layer.

9. The measurement system according to claim 6, the system further comprising a laser array that includes a plurality of laser elements arranged in matrix, each laser element emitting a laser beam perpendicular to the back surface of the photoconductive layer.

10. The measurement system according to claim 6, the system further comprising an X-Y positioner for controlling the horizontal position of the two-dimensional sensor for changing a location of the laser-irradiated spot on the sensor.

* * * * *